United States Patent [19]

Nesmeyanov et al.

[11] 4,109,660
[45] Aug. 29, 1978

[54] METHOD OF TOOTH ANESTHETIZING DURING DENTAL TREATMENT AND DEVICE FOR EFFECTING SAME

[76] Inventors: Nikolai Alexandrovich Nesmeyanov, Inzhenernaya ulitsa, 46, Nalchik; Ivan Alexandrovich Nesmeyanov, ulitsa Kuusinena, 25, kv. 31, Moscow; Anatoly Alexandrovich Nesmeyanov, Kaluzhsky pereulok, 7, kv. 93, Leningrad, all of U.S.S.R.

[21] Appl. No.: 756,847

[22] Filed: Jan. 5, 1977

[51] Int. Cl.² .............................................. A61N 1/34
[52] U.S. Cl. .............................. 128/419 R; 128/409
[58] Field of Search ............... 128/409, 410, 419 R, 128/420, 172.1

[56] References Cited

U.S. PATENT DOCUMENTS

| 493,723 | 3/1893 | Horton, Jr. | 128/409 |
| 535,905 | 3/1895 | Horton, Jr. et al. | 128/409 |
| 2,866,461 | 12/1958 | Suzuki | 128/419 R |
| 3,955,583 | 5/1976 | Horauf | 128/420 R |

FOREIGN PATENT DOCUMENTS 712,703  7/1954  United Kingdom ..................... 128/409

OTHER PUBLICATIONS

Nesmeyanov et al., "An Electric Dental . . . Current", Biomedical Eng, vol. 10, No. 2, pp. 107–108 — Mar.-Apr. 1976.

Primary Examiner—Robert W. Michell
Assistant Examiner—Lee S. Cohen
Attorney, Agent, or Firm—Steinberg & Blake

[57] ABSTRACT

Stablized d.c. voltage signals are applied to a tooth in the course of treatment, preferably, through the electric circuit between the ear lobe and the tooth. The voltage is selected between 1.7 and 2.2 volts. Electroanesthesia is induced by electric signals arriving from a d.c. voltage source which generates voltage of 1.7 to 2.2 volts. The positive terminal of the source is connected to the stomatological instrument, whereas the negative terminal is connected to an ear lobe.

12 Claims, 1 Drawing Figure

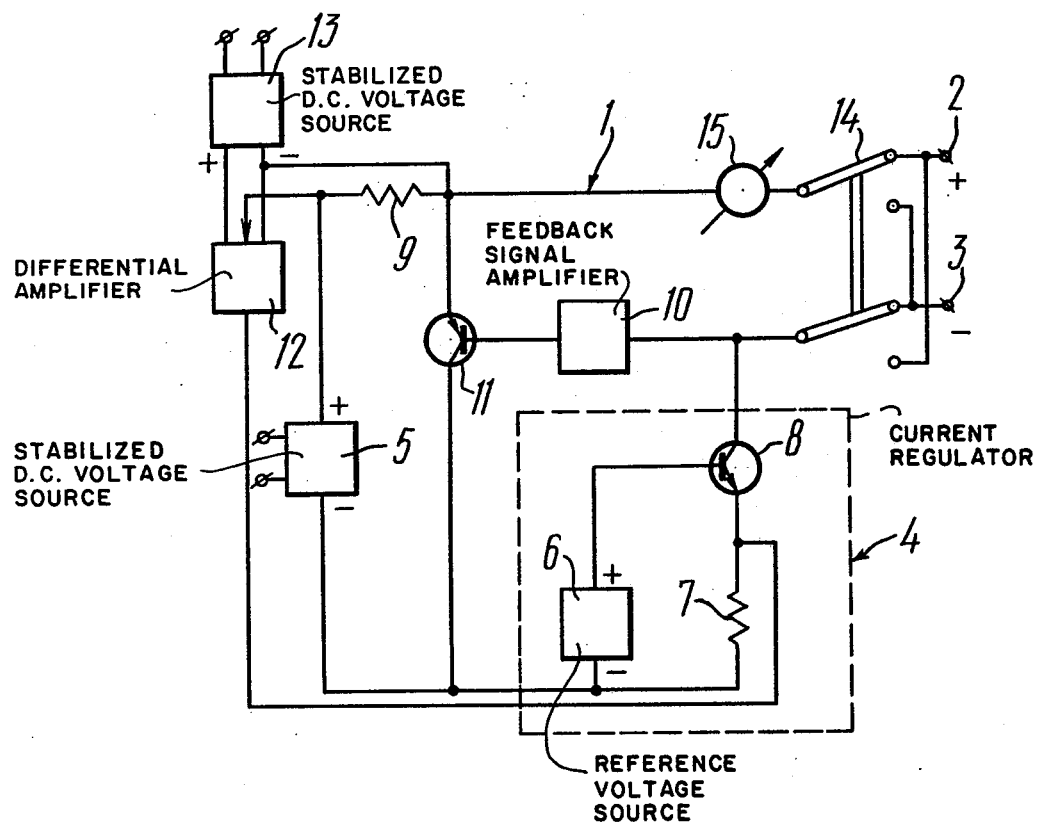

METHOD OF TOOTH ANESTHETIZING DURING DENTAL TREATMENT AND DEVICE FOR EFFECTING SAME

The present invention relates to medicine and, more particularly, to anesthetic techniques and devices. Still more specifically, the invention is related to a method of anesthetizing a tooth in the course of treatment and a device for effecting same. The invention is especially advantageous for anesthetizing teeth in the course of treatment at stomatological clinics.

At one time or another, most people seek aid in stomatological clinics. Some 90 percent of the Soviet Union's population is regularly inspected and treated by dentists. Most people are highly sensitive to pain in the course of treatment. The dentist's intervention is especially painful when the patient has a toothache. In view of this, extensive research has been carried out in anesthetizing techniques and devices.

Researchers are particularly interested in looking for anesthetizing techniques to replace anesthetics, such as novocain. The reasons for this are obvious. On the one hand, such anesthetics do not necessarily ensure a required degree of anesthesia; on the other hand, when the anesthetic effect wears off, they account for unpleasant sensations due to their toxicity.

The foregoing factors have led to a comparatively extensive use of electroanesthesia, i.e., application of electric current to tissues of a tooth being treated. Such technique is advantageous in that it is non-toxic and, in principle, makes it possible to attain any degree of anesthesia. In addition, electroanesthesia is a fast-acting technique and, as is highly important, makes it possible to eliminate rapidly the effects of anesthesia.

According to one known method of electroanesthesia used in the course of therapeutic dental treatment, the tooth being treated is acted upon by stabilized d.c. voltage signals. Of course, such signals must be harmless to the organism.

It has been established that such electric signals do produce the anesthetizing effect. However, the current magnitude has to be selected during the course of treatment.

Normally, any existing electroanesthesia device includes a d.c. source, a stabilizer which, as a rule, is built around a silicon transistor, a working electrode, an auxiliary electrode, and a polarity reversing switch. The positive electrode is connected to the dental instrument, such as for example, the drill. The negative electrode is connected to the patient's ear lobe. It must be pointed out that devices of the type under review have a number of drawbacks. An important drawback resides in the fact that in order to attain anesthesia, the dentist must tentatively work on the aching tooth of each new patient in order to select the current magnitude that provides the surest anesthetizing effect. Such trials, however, are hard on the patient, because they are performed with the rotating drill. The pain is aggravated if the patient is already suffering from toothache. Besides, this means a considerable waste of time, especially keeping in mind that a specific current magnitude must be selected not only for each patient but also for each tooth. Finally, such a device does not rule out a surge of pain due to a random change in the resistance of the anesthetized zone.

It is the main object of the present invention to provide an electroanesthesia technique which makes any adjustment unnecessary and eliminates pain in the course of treatment.

It is another object of the intention to speed up the treatment due to faster anesthesia.

It is still another object of the invention to raise the effectiveness of anesthesia.

It is yet another object of the invention to provide an electroanesthesia device for dental treatment which assures fast, reliable and effective anesthesia.

The invention essentially aims at selecting such parameters of the electric signal which induces anesthesia, which eliminates pain in the course of preparatory steps and the treatment itself, and which provides an appropriate dental treatment device.

The foregoing and other objects are attained in that according to the invention, a tooth being treated is acted upon by stabilized d.c. voltage.

The major advantage of the present invention lies in the fact that it eliminates adjustment of the anesthesia apparatus and, consequently, pain which such adjustment may inflict. Besides, the invention eliminates pain due to changes in the electric resistance of the tooth, which is often the case when using the conventional method of electroanesthesia.

It is expedient that the circuit for the stabilized voltage signal should be composed of a part of the patient's body and the tooth so that the voltage drop should occur in the tooth and amount to about 1.8 V.

Good results are attained when the electric signal passes through the ear lobe to the tooth and when the voltage applied to the tooth is 1.7 to 2.2 volts; the best results are attained when the voltage is 1.8 V.

The device for carrying out the proposed method comprises an electric signal source which is a stabilized d.c. voltage source generating voltage in the range of 1.7 to 2.2 volts. The positive terminal of the source is connected to the dental instrument, while the negative terminal is coupled to the patient's ear lobe.

The attached drawing is a schematic representation of the proposed device for anesthetizing a tooth in the course of therapeutic treatment. The device comprises a stabilized d.c. voltage source 1 having a positive terminal 2 and a negative terminal 3. The positive terminal 2 is to be connected to a dental instrument, for example, a metal drill tip (not shown). The negative terminal 3 may be an ordinary clip which is attached, for example, to the patient's ear lobe.

The electric signal source generates stabilized voltage of 1.7 to 2.2 volts.

The source of FIG. 1 includes a current regulator 4 having a negative feedback circuit whose purpose, design and operating principle will be discussed in detail below.

The current regulator 4 is fed from any stabilized d.c. voltage source 5.

The regulator 4 includes a reference voltage source 6. Placed in parallel with the reference voltage source 6 is a resistor 7. The output of the current regulator 4 is a transistor 8 whose collector is connected to the negative terminal 3. The positive terminal 2 is connected to that of the power source 5 via a resistor 9 incorporated in the negative feedback circuit. The parameters of the reference voltage source 6 and resistor 7 of the regulator 4 are selected to meet the requirement that when there is no negative feedback, the magnitude of the current flowing through the external circuit must never be in excess of maximum permissible values prescribed for dental anesthesia. This will be discussed in greater detail below and is meant to eliminate undesirable effects due to passage of a high current through nervous tissue.

The maximum permissible values of anesthetizing current are different in different countries. For example, in the USSR the maximum permissible value is 30 microamperes, whereas in France it may be as high as 60 microamperes.

Besides, it is desirable that the reference voltage source should be a stabilizing element selected from the group including avalanche diodes, stabistors, series connected emitter-base junctions, diodes, etc. These require a minimum supply current and make it possible to use the resistor 7 whose resistance is several orders lower than that of the insulation (for example, the resistance of the board whereupon the elements of the device are mounted) under most unfavorable climatic conditions, such as elevated temperature and humidity, etc.

The embodiment under review incorporates the emitter-base junction of two transistors which are identical with the transistor 8. The current is on the order of 1 mA. Thus the current through the external circuit is derived from this equation:

$$I_1 = \frac{2U_2 - U_2}{R_7} \qquad (1),$$

where
$I_1$ is the current through the external circuit of the device, for example 30 microamperes;
$U_2$ is the voltage across the emitter-base junction of the transistors used in the device (this voltage normally amounts to 0.6 to 0.8 V);
$R_7$ is the resistance of the resistor 7.

It is inferred from the above that the resistance of the resistor 7 is:

$$R_7 \approx \frac{2U_2 - U_2}{I_1} = \frac{2.0.6 - 0.6}{30.10^{-6}} = 20 \text{ kilohms}.$$

If the maximum permissible current magnitude is 60 microamperes, the resistance of the resistor 7 is: $R_7 \approx 10$ kilohms.

Thus it is possible to ensure any operating conditions of the current regulator at minimum values of leakage currents, which are significantly less than the minimum anesthesia current values.

The negative feedback circuit is intended for two purposes. First, it is to stabilize voltage across the collector of the transistor 8, which is necessary to ensure stable operation of the current regulator 4; a minimum value of this voltage makes it possible to reduce the values of uncontrolled collector currents to a level which is much lower than that of anesthesia current with the transistor 8 operating in the linear mode. It should be borne in mind that stabilized voltage across the collector of the transistor 8 is crucial for automatic adjustment of the device. This is a parameter with regard to which the anesthesia voltage is calculated. Keeping this parameter constant is essential to produce the anesthetizing effect. The value of the collector voltage of the transistor 8 is determined by selecting the circuitry and components of a feedback signal amplifier 10 whose input is connected to the collector of the transistor 8, while its output is connected to the base of a transistor 11. The transistor 11, the feedback signal amplifier 10 and the resistor 9 of the power source 5 makes up what is referred to as a parallel d.c. voltage stabilizer whose output voltage is stable and equal to the sum total of the voltages of the reference voltage source 6 and the collector-base junction of the transistor 8.

The second and main purpose of the negative feedback circuit is to ensure stable voltage at the output of the device. This is attained with the aid of a compensating circuit means including a differential amplifier 12 having a stabilized d.c. voltage source 13 of its own. The function of the differential amplifier 12 can be performed by any other similar unit. The selection of the differential amplifier is accounted for by its high noise immunity. Besides, it ensures a high temperature stabilization level of the output voltage, which makes it possible to dispense with other circuit components. Connected to the input of the differential amplifier 12 is the resistor 9 which serves as a voltage sensor for the negative feedback circuit. The output of the differential amplifier 12 is connected to the emitter of the transistor 8.

Incorporated in the collector circuit of the transistor 8 of the current regulator 4 is a polarity reversing switch 14 which is to exclude adaptation to electroanesthesia. In most cases, however, it is unnecessary to use the switch 14.

Interposed between the polarity reversing switch 14 and the resistor 9 is a pointer-type measuring instrument 15 which serves as an indicator during the course of operation. The instrument 15 can also be used to adjust and calibrate the device during manufacture whenever such operations are necessary.

In order to ensure sufficient operating stability of the device, the function of the power sources 5 and 13 is to be performed by stabilized voltage sources whose output parameters are selected so as to ensure economical and effective operation of the current regulator 4, the differential amplifier 12 and the anesthetizing device as a whole. The power source 5 is built around an avalanche diode having a stabilization voltage of 8.5 to 10 V. The voltage source 13 is built around two series connected avalanche diodes of the same type with a total output voltage of 17 to 20 V.

The proposed device operates as follows. The device is hooked up to alternating current mains, for example, with a voltage of 220 V. By switching on a toggle switch (not shown), the voltage is applied to a power transformer (not shown). Alternating voltage is induced at the output of said transformer, in two galvanically disconnected secondary windings thereof. The value of said d.c. voltage is selected so as to ensure economic and effective operation of the whole device. In the case under review, the d.c. voltage at the output windings of the transformer (not shown) is selected to be 32 V to feed the power source 5 of the current regulator 4, and 36 V to feed the power source 13 of the differential amplifier 12. Said voltages are applied to conventional bridge rectifiers, filtered by RC filters (not shown so as not to encumber the accompanying drawing with minor details), and applied to the stabilized sources 5 and 13.

The dentist attaches the negative terminal (the clip) 3 to the patient's ear lobe. The positive terminal is connected to the dental instrument, for example, the drill tip which must be insulated from the dentist's hand, for example, by a rubber glove, etc.

When the tooth has been carefully cleaned, the dentist may start working on it by using conventional techniques.

It is absolutely necessary that naked parts of the instrument should contact the tooth only in the treatment zone since otherwise there will be a leakage current, and the current passing through the nerve endings will be insufficient for anesthesia.

The device of this invention is to produce a stabilized d.c. voltage signal of 1.7 to 2.2 volts when the negative terminal 3 is connected to the patient's ear lobe. 1.8 V is the optimum value which ensures a high degree of anesthesia.

It must be pointed out that when the negative electrode is connected to other parts of the body, for example, an arm or lip, the magnitude of d.c. voltage may be beyond the range of 1.7 to 2.2 V.

However, a stabilized voltage value, which is prescribed for a certain electric circuit, for example, lip--tooth, arm-tooth, etc., ensures effective anesthesia without any additional adjustment in the course of treatment. This is the basic advantage of the present invention, keeping in mind that the conventional method of electroanesthesia requires current adjustments during treatment, whereby the effectiveness of anesthesia is impaired.

The optimum or selected d.c. voltage is maintained as follows.

The selection in the above-mentioned manner of the parameters of the components 6 and 7 of the current regulator 4 results in the fact that with short-circuiting of the output terminals or with load resistance of less than 80 to 61 kiloohms the current magnitude at the device's output is never in excess of the maximum permissible level prescribed on the basis of safety requirements (in the present case this level is 30 microamperes), although by varying the resistance of the resistor 7 it is possible to achieve any higher or lower level.

Under the above-mentioned conditions, the negative feedback circuit means, which includes the amplifier 10, the transistor 11, the resistor 9 and the power source 5, ensures constant stabilized voltage across the collector of the transistor 8 of the current regulator 4. This is done as follows. When the output voltage of the amplifier 10 incorporated in the feedback circuit tends to increase, as compared to a prescribed value, there is an increase in the amplifier current, which leads to an increase in the emitter current of the transistor 11. The latter increases the voltage drop at the resistor 9, which, in turn, ensures constant current in the collector of the transistor 8 because the voltage across the output of the power source 5 is constant and stabilized.

The foregoing process of maintaining voltage across the collector of the transistor 8 takes place in normal operating conditions, i.e., when voltage across the output terminals of the device is maintained at a constant prescribed level which in the present case is 1.8 V. If this voltage goes up, for example, by Δ U, which is due to changes in the resistance of the ear lobe-tooth circuit (said resistance normally fluctuates from 60 × 10³ to 1.8 × 10⁶ ohms), the voltage drop at the resistor 9 goes down by the same value because all the other voltages are stabilized, including those of the power source 5, the reference voltage source 6, and the collector of the transistor 8. The voltage drop across the resistor 9 actuates the differential amplifier 12 so that its output current is of a magnitude which ensures a constant voltage drop across the resistor 7, determined by this expression:

$$U_{R_7} = U_3 - U_2,$$

where
$U_{R_7}$ is the voltage drop across the resistor 7;
$U_3$ is the output voltage of the reference voltage source 6;
and
$U_2$ is the voltage across the emitter-base junction of the transistor 8.

This, in turn, reduces the current passing through the variable load circuit (the resistance of the ear lobe--tooth circuit), whereby the chief requirement for effective operation of the anesthesia device is complied with, i.e., $(R_4 \pm \Delta R_4)(I_1 \pm \Delta I_1) = 1.8$ V $=$ const, where $R_4$ is the resistance of the ear lobe-tooth circuit;
$\Delta R_4$ is the deviation in the resistance of the ear lobe--tooth circuit;
$I_1$ is the controlled current of the regulator 4 through the collector circuit of the transistor 8; and
$\Delta I_1$ is the deviation in the collector current of the transistor 8 caused by the negative feedback circuit.

The above expression indicates that with a change in the load resistance within a broad range from 60÷80 to 1.8÷2 kilohms the voltage across the output terminals remains constant, which accounts for effective anesthesia; at the same time the current magnitudes may change from a few microamperes to scores of microamperes.

What is claimed is:

1. In a device for anesthetizing a tooth in the course of dental treatment, positive and negative terminals adapted respectively to be connected with a dental instrument and a part of a patient's body such as an ear lobe, for providing a given voltage drop in the patient's body, a stabilized d.c. voltage source having a pair of terminals, and electrical circuit means connecting said terminals of said voltage source respectively to said positive and negative terminals, said circuit means including a current regulator means which includes a transistor having a collector electrically connected to said negative terminal by said circuit means, and said circuit means including a negative feedback circuit means formed in part by said voltage source and connected between the latter and said collector for maintaining a constant current therein.

2. The combination of claim 1 and wherein a compensating circuit means is electrically connected between said negative feedback circuit means and said current regulator means for compensating for changes in the resistance of the body of the patient between said positive and negative terminals.

3. The combination of claim 2 and wherein said compensating circuit means has its own stabilized d.c. voltage source.

4. The combination of claim 1 and wherein said negative feedback circuit means includes in addition to said voltage source, a resistor connected between one of said terminals thereof and said positive terminal, a second transistor connected between said resistor and said current regulator means, and a feedback signal amplifier connected between said second transistor and said collector of said transistor of said current regulator means.

5. The combination of claim 4 and wherein said current regulator means includes in addition to said transistor thereof a reference voltage source and a resistor connected in parallel therewith, said transistor of said current regulator means including a base connected to said reference voltage source and an emitter connected to said resistor which is in parallel with said reference voltage source.

6. The combination of claim 5 and wherein said second transistor and the terminal of said voltage source which is not connected to said resistor of said negative feedback circuit means are both electrically connected to a junction between the parallel-connected reference voltage source and resistor of said current regulator means.

7. The combination of claim 6 and wherein a compensating circuit means is electrically connected between said current regulator means and said negative feedback circuit means for compensating for a change in the resistance of the patient's body between said positive and negative terminals.

8. The combination of claim 7 and wherein said compensating circuit means includes a differential amplifier having its own source of stabilized d.c. voltage, said differential amplifier having an input to which said resistor of said negative feedback circuit means is connected to form an input for said differential amplifier, and the latter having an output connected to said current regulator means between said resistor thereof and said emitter of said transistor thereof.

9. In a method of electroanesthetizing a tooth during the course of dental treatment, the steps of connecting a positive terminal to a dental instrument to be applied to a tooth while connecting a negative terminal to a part of the patient's body, supplying said terminals through a circuit with energy from a stabilized d.c. voltage source which will provide between the terminals through a part of the patient's body a voltage drop of between 1.7 and 2.2 V, connecting into said circuit between said voltage source and terminals a current regulator having a transistor which includes a collector connected electrically to said negative terminal, and maintaining the current in said collector constant by way of a negative feedback circuit which includes said voltage source.

10. In a method as recited in claim 9 and wherein the stabilized d.c. voltage source and the other electrical components are selected to provide in the patient's body between said positive and negative terminals a voltage drop of 1.8 V.

11. In a method as recited in claim 9 and including the step of connecting the negative terminal to the patient's ear lobe.

12. In a method as recited in claim 9 and including the step of connecting to said negative feedback circuit and said current regulator a compensating circuit for compensating for changes in the resistance of the patient's body.

* * * * *